(12) United States Patent
Thoe et al.

(10) Patent No.: US 9,089,367 B2
(45) Date of Patent: Jul. 28, 2015

(54) PATIENT EYE LEVEL TOUCH CONTROL

(75) Inventors: David A. Thoe, Laguna Hills, CA (US); John Koontz, Corona, CA (US); Mikhail Boukhny, Laguna Nigel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1050 days.

(21) Appl. No.: 13/081,666

(22) Filed: Apr. 7, 2011

(65) Prior Publication Data

US 2011/0251548 A1    Oct. 13, 2011

Related U.S. Application Data

(60) Provisional application No. 61/321,998, filed on Apr. 8, 2010.

(51) Int. Cl.
    *A61B 19/00*     (2006.01)
    *A61M 1/00*     (2006.01)
    *A61F 9/007*     (2006.01)

(52) U.S. Cl.
    CPC ............... *A61B 19/56* (2013.01); *A61F 9/007* (2013.01); *A61M 1/0058* (2013.01); *A61B 2019/4836* (2013.01); *A61B 2019/4857* (2013.01); *A61M 2205/3344* (2013.01); *A61M 2205/505* (2013.01)

(58) Field of Classification Search
    CPC ........... A61B 19/56; A61B 2019/4836; A61B 2019/4857; A61F 9/007; A61M 1/0058; A61M 2205/3344; A61M 2205/505
    USPC ............... 604/30–31, 35, 118, 119, 120, 121; 606/4
    See application file for complete search history.

(56) References Cited

U.S. PATENT DOCUMENTS

| | | | |
|---|---|---|---|
| 2,450,062 A | 9/1948 | Voss et al. | |
| 3,239,872 A | 3/1966 | Kitrell | |

(Continued)

FOREIGN PATENT DOCUMENTS

| | | |
|---|---|---|
| BR | 8504205 | 4/1987 |
| CN | 2273269 | 1/1998 |

(Continued)

OTHER PUBLICATIONS

European Searching Authority, Extended Supplementary European Search Report, European Patent Application No. 11766694.1, Publication No. 2555725, Published Feb. 13, 2013, 5 pages.

(Continued)

*Primary Examiner* — Andrew Gilbert

(57) ABSTRACT

In various embodiments, a surgical console may include a sensor strip with sensor strip sensors (e.g., field effect or capacitive sensors) offset vertically and configured to receive an input from a user corresponding to a vertical height of a patient's eyes relative to the surgical console. The surgical console may use the input from the sensor strip to determine a patient eye level (PEL) relative to a surgical console component and then use the PEL and the at least one component in controlling operation of at least one of a source of irrigation or a source of aspiration during an ophthalmic procedure. The surgical console may further include a plurality of visual indicators positioned relative to at least two of the plurality of sensor strip sensors and configured to be illuminated to correspond to a sensor detecting the touch input.

18 Claims, 8 Drawing Sheets

(56) References Cited

U.S. PATENT DOCUMENTS

| | | |
|---|---|---|
| 3,652,103 A | 3/1972 | Higgs |
| 3,818,542 A | 6/1974 | Jones |
| 3,890,668 A | 6/1975 | Stosberg et al. |
| 3,920,014 A | 11/1975 | Banko |
| 4,025,099 A | 5/1977 | Virden |
| 4,110,866 A | 9/1978 | Ishii |
| 4,143,442 A | 3/1979 | Harlang |
| 4,550,221 A * | 10/1985 | Mabusth ............... 178/18.06 |
| 4,550,808 A | 11/1985 | Folson |
| 4,616,888 A | 10/1986 | Peterman |
| 4,633,544 A | 1/1987 | Hicks |
| 4,669,580 A | 6/1987 | Neville |
| 4,675,485 A | 6/1987 | Paukert |
| 4,677,706 A | 7/1987 | Screen |
| 4,744,536 A | 5/1988 | Bancalari |
| 4,811,966 A | 3/1989 | Singleton |
| 4,941,552 A | 7/1990 | Screen |
| D325,086 S | 3/1992 | Charles et al. |
| 5,112,019 A | 5/1992 | Metzler et al. |
| 5,242,035 A | 9/1993 | Lange |
| 5,249,121 A | 9/1993 | Baum et al. |
| 5,273,043 A | 12/1993 | Ruike |
| 5,280,789 A * | 1/1994 | Potts ............... 600/486 |
| 5,315,290 A | 5/1994 | Moreno et al. |
| D352,106 S | 11/1994 | Fanney et al. |
| 5,456,336 A | 10/1995 | Bopp |
| 5,642,392 A * | 6/1997 | Nakano et al. ............... 378/38 |
| 5,650,597 A * | 7/1997 | Redmayne ............... 178/18.06 |
| 5,702,117 A | 12/1997 | Geelhoed |
| 5,752,520 A * | 5/1998 | Bisnaire et al. ............... 600/561 |
| 5,766,146 A | 6/1998 | Barwick, Jr. |
| 5,788,688 A | 8/1998 | Bauer et al. |
| 5,800,383 A | 9/1998 | Chandler et al. |
| 5,810,765 A | 9/1998 | Oda |
| 5,823,302 A | 10/1998 | Schweninger |
| 5,827,149 A | 10/1998 | Sponable |
| 5,830,180 A | 11/1998 | Chandler et al. |
| 5,836,081 A * | 11/1998 | Orosz, Jr. ............... 33/290 |
| 5,857,685 A | 1/1999 | Phillips et al. |
| 5,859,629 A | 1/1999 | Tognazzini |
| 5,876,016 A | 3/1999 | Urban et al. |
| 5,880,538 A | 3/1999 | Schulz |
| 5,964,313 A | 10/1999 | Guy |
| 5,988,323 A | 11/1999 | Chu |
| 6,024,720 A | 2/2000 | Chandler et al. |
| 6,034,449 A | 3/2000 | Sakai et al. |
| 6,047,634 A | 4/2000 | Futsuhara et al. |
| 6,055,458 A | 4/2000 | Cochran et al. |
| 6,109,572 A | 8/2000 | Urban et al. |
| 6,232,758 B1 | 5/2001 | Konda et al. |
| 6,251,113 B1 | 6/2001 | Appelbaum et al. |
| 6,267,503 B1 * | 7/2001 | McBride ............... 378/206 |
| 6,276,485 B1 | 8/2001 | Eriksson et al. |
| D447,567 S | 9/2001 | Murphy et al. |
| 6,357,765 B1 | 3/2002 | Heien |
| 6,409,187 B1 | 6/2002 | Crow, Jr. |
| 6,429,782 B2 | 8/2002 | Pavatich et al. |
| D467,001 S | 12/2002 | Buczek et al. |
| 6,501,198 B2 | 12/2002 | Taylor et al. |
| 6,503,208 B1 | 1/2003 | Skovlund |
| 6,530,598 B1 | 3/2003 | Kirby |
| 6,532,624 B1 | 3/2003 | Yang |
| 6,587,750 B2 | 7/2003 | Gerbi et al. |
| 6,590,171 B1 | 7/2003 | Wolf et al. |
| 6,619,438 B1 | 9/2003 | Yang |
| 6,626,445 B2 | 9/2003 | Murphy et al. |
| 6,662,404 B1 | 12/2003 | Stroh et al. |
| 6,678,917 B1 | 1/2004 | Winters et al. |
| 6,749,538 B2 | 6/2004 | Slawinski et al. |
| 6,824,539 B2 | 11/2004 | Novak |
| 6,854,568 B2 | 2/2005 | Kun-Tsai |
| 6,899,694 B2 * | 5/2005 | Kadziauskas et al. ............... 604/35 |
| 6,944,910 B2 | 9/2005 | Pauls |
| 6,969,032 B2 | 11/2005 | Olivera et al. |
| 6,971,617 B2 | 12/2005 | Nguyen |
| 7,065,812 B2 | 6/2006 | Newkirk et al. |
| 7,100,716 B2 | 9/2006 | Engels et al. |
| D550,362 S | 9/2007 | Olivera et al. |
| 7,454,839 B2 | 11/2008 | Della Bona et al. |
| 7,509,747 B2 | 3/2009 | Sudou et al. |
| 7,685,660 B2 | 3/2010 | Chinn |
| 7,878,289 B2 | 2/2011 | Standke |
| 8,542,203 B2 * | 9/2013 | Serban et al. ............... 345/173 |
| 2001/0023331 A1 | 9/2001 | Kanda et al. |
| 2004/0119484 A1 | 6/2004 | Basir et al. |
| 2004/0226187 A1 | 11/2004 | Bruntz et al. |
| 2005/0004559 A1 | 1/2005 | Quick et al. |
| 2005/0068417 A1 * | 3/2005 | Kreiner et al. ............... 348/143 |
| 2005/0088417 A1 | 4/2005 | Mulligan |
| 2005/0230575 A1 | 10/2005 | Zelenski et al. |
| 2005/0234441 A1 | 10/2005 | Bisch et al. |
| 2006/0031989 A1 | 2/2006 | Graham et al. |
| 2006/0113733 A1 | 6/2006 | Kazaoka |
| 2006/0149426 A1 | 7/2006 | Unkrich et al. |
| 2006/0267295 A1 | 11/2006 | You |
| 2007/0051566 A1 | 3/2007 | Marlow |
| 2007/0124858 A1 | 6/2007 | Ahlman |
| 2008/0033361 A1 | 2/2008 | Evans et al. |
| 2008/0114290 A1 * | 5/2008 | King et al. ............... 604/30 |
| 2008/0126969 A1 | 5/2008 | Blomquist |
| 2008/0147023 A1 | 6/2008 | Hopkins |
| 2008/0189173 A1 | 8/2008 | Bakar et al. |
| 2008/0223650 A1 | 9/2008 | Standke |
| 2009/0013780 A1 | 1/2009 | Gao |
| 2009/0036271 A1 | 2/2009 | Brand et al. |
| 2009/0040181 A1 | 2/2009 | Darnell et al. |
| 2009/0045021 A1 | 2/2009 | Einbinder |
| 2009/0069799 A1 | 3/2009 | Daw et al. |
| 2009/0090434 A1 | 4/2009 | Brand et al. |
| 2009/0143734 A1 | 6/2009 | Humayun et al. |
| 2009/0231095 A1 | 9/2009 | Gray |
| 2009/0289431 A1 | 11/2009 | Geeslin |
| 2010/0019200 A1 * | 1/2010 | Chi et al. ............... 252/301.4 H |
| 2010/0049119 A1 | 2/2010 | Norman et al. |
| 2011/0247173 A1 | 10/2011 | Nguyen et al. |
| 2011/0251548 A1 | 10/2011 | Koontz et al. |

FOREIGN PATENT DOCUMENTS

| | | |
|---|---|---|
| DE | 2102508 B2 | 6/1973 |
| DE | 3016615 A1 | 11/1981 |
| DE | 3039611 A1 | 4/1982 |
| DE | 3203886 A1 | 9/1983 |
| DE | 8910606 U1 | 10/1989 |
| DE | 4344187 A1 | 6/1995 |
| DE | 19504073 C1 | 8/1996 |
| DE | 10047006 C2 | 4/2002 |
| DE | 20308670 U1 | 2/2004 |
| DE | 10332823 A1 | 2/2005 |
| DE | 202005016310 U1 | 1/2006 |
| DE | 202007008797 U1 | 8/2007 |
| DE | 102006049071 B3 | 11/2007 |
| DE | 102008015505 A1 | 2/2009 |
| DE | 102007053444 A1 | 5/2009 |
| DE | 102009058919 A1 | 6/2011 |
| EP | 0701917 A1 | 3/1996 |
| EP | 0979741 A2 | 2/2000 |
| EP | 1016580 A1 | 7/2000 |
| EP | 1024071 A1 | 8/2000 |
| EP | 1180473 A1 | 2/2002 |
| EP | 0901388 B1 | 1/2003 |
| EP | 1964750 A1 | 9/2008 |
| EP | 2106986 A1 | 10/2009 |
| EP | 1016578 B1 | 3/2010 |
| EP | 2173154 B1 | 1/2011 |
| EP | 2292202 A2 | 3/2011 |
| ES | 2285964 | 11/2007 |
| FR | 2648101 | 12/1990 |
| FR | 2799410 | 4/2001 |
| FR | 2880700 A1 | 7/2006 |
| GB | 210851 | 2/1924 |
| GB | 767159 | 1/1957 |
| GB | 2061105 | 5/1981 |
| GB | 2132478 | 7/1984 |

(56) References Cited

FOREIGN PATENT DOCUMENTS

| | | | |
|---|---|---|---|
| GB | 2260195 A | | 4/1993 |
| GB | 2260622 A | | 4/1993 |
| GB | 2441303 A | | 3/2008 |
| JP | 02-107245 | * | 4/1990 |
| JP | 03-062902 | | 3/1991 |
| JP | 03-190919 | | 8/1991 |
| JP | 03-252266 | | 11/1991 |
| JP | 04-063328 | | 2/1992 |
| JP | 09-058203 | | 3/1997 |
| JP | 09-113071 | | 5/1997 |
| JP | 10-297206 | | 11/1998 |
| JP | 11-169411 | | 6/1999 |
| JP | 11-244339 | | 9/1999 |
| JP | 2001-001703 | | 1/2001 |
| JP | 2001-058503 | | 3/2001 |
| JP | 2002-312116 | | 10/2002 |
| JP | 2003-220803 | | 8/2003 |
| JP | 2005-162113 | | 6/2005 |
| JP | 2005-296606 | | 10/2005 |
| JP | 2006-341670 | | 12/2006 |
| JP | 2007-137305 | | 6/2007 |
| JP | 2009-512971 | | 3/2009 |
| JP | 2010-508104 | | 3/2010 |
| JP | 2010-088490 | | 4/2010 |
| WO | WO/98/25556 | * | 6/1998 |
| WO | WO 98/25556 A1 | | 6/1998 |
| WO | WO 00/12150 A1 | | 3/2000 |
| WO | WO 00/18012 A1 | | 3/2000 |
| WO | WO 02/043571 A2 | | 6/2002 |
| WO | WO/2006/073400 | * | 6/2002 |
| WO | WO 02/043571 A3 | | 4/2003 |
| WO | WO 03/093408 A1 | | 11/2003 |
| WO | WO 2004/017521 A1 | | 2/2004 |
| WO | WO 2004/082554 A2 | | 9/2004 |
| WO | WO 2004/082554 A3 | | 3/2005 |
| WO | WO 2006/073400 A1 | | 7/2006 |
| WO | WO 2008/052752 A1 | | 5/2008 |
| WO | WO 2008/053485 A1 | | 5/2008 |
| WO | 2009/021836 A1 | | 2/2009 |
| WO | WO/2009/021836 | * | 2/2009 |
| WO | WO 2009/073691 A2 | | 6/2009 |
| WO | WO 2009/073769 A2 | | 6/2009 |
| WO | WO 2009/073691 A3 | | 7/2009 |
| WO | WO 2009/073769 A3 | | 7/2009 |
| WO | WO 2010/020200 A1 | | 2/2010 |
| WO | WO 2010/027255 A1 | | 3/2010 |
| WO | WO 2010/027255 A8 | | 3/2010 |
| WO | WO 2011/126596 A1 | | 10/2011 |
| WO | WO 2011/126597 A1 | | 10/2011 |
| WO | WO 2011/127231 A1 | | 10/2011 |

OTHER PUBLICATIONS

International Searching Authority, Written Opinion of the International Searching Authority, International Application No. PCT/US2011/023107, Mar. 31, 2011, 7 pages.
International Searching Authority, International Search Report, International Application No. PCT/US2011/023107, Mar. 31, 2011, 2 pages.
International Searching Authority, International Search Report, International Application No. PCT/US11/23103, Mar. 30, 2011, 2 pages.
International Searching Authority, Written Opinion of the International Searching Authority, International Application No. PCT/US11/23103, Mar. 30, 2011, 4 pages.
International Searching Authority, International Search Report, PCT/US2011/031500, Jun. 16, 2011, 2 pages.
International Searching Authority, Written Opinion of the International Searching Authority, PCT/US2011/031500, Jun. 16, 2011, 6 pages.
Steinco brochure accessed through http://web.archive.org/web/20080731183316/http://www.steinco.de/service/downloads. aspx?id=6901 & accessed from page http://web.archive.org/web/20080731188316/http://www.steinco.de/en/Castors_Hospital. aspx—original date believed to be Jul. 31, 2008, 2 pages.
http://web.archive.org/web/20090526022232/http://www.touchsensor.com/engineers.html?bcsi_scan_0A8B7FA59D377CC3=w1 . . . (web archive dated May 26, 2009) (2 pages).
http://web.archive.org/web/20090322184659/http://www.touchsensor.com/technology_switch.html (web archive dated Mar. 22, 2009) (2 pages).

* cited by examiner

PATIENT EYE LEVEL TOUCH CONTROL

PRIORITY CLAIM

This application claims the benefit of priority of U.S. Provisional Patent Application Ser. No. 61/321,998 titled "Patient Eye Level Touch Control", filed on Apr. 8, 2010, whose inventors are John Koontz, David Thoe, and Mikhail Boukhny, which is hereby incorporated by reference in its entirety as though fully and completely set forth herein.

FIELD OF THE INVENTION

The present invention generally pertains to surgical consoles. More particularly, but not by way of limitation, the present invention pertains to patient eye level determination for surgical consoles.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens. Different surgical procedures performed on the eye may require precise control of fluid pressure being delivered to the eye. The height of a sensor or fluid source above (or below) a patient's eye may affect pressure measurements and/or the pressure of fluid being delivered from the fluid source to the eye. Current surgical systems may require a user to estimate the distance between, for example, an aspiration sensor, and a user's eyes and type that data into the console.

SUMMARY

In various embodiments, a surgical console may include a sensor strip with sensor strip sensors (e.g., field effect or capacitive sensors) offset vertically and configured to receive an input from a user corresponding to a vertical height of a patient's eyes relative to the surgical console. The surgical console may further include at least one component (e.g., an aspiration sensor) configured to be used during an ophthalmic procedure. In some embodiments, the surgical console may use the input from the sensor strip to determine a patient eye level (PEL) relative to the at least one component and then use the PEL and the at least one component in controlling, for example, irrigation or aspiration during the ophthalmic procedure. In some embodiments, the PEL may be a perpendicular distance between the patient's eyes and a line, parallel to the ground/floor, that intersects the at least one component of the surgical console. The surgical console may further include visual indicators positioned relative to the sensor strip sensors to be illuminated in response to detected touch input. In some embodiments, the sensor strip sensors and/or visual indicators may be arranged along a curved line on the surgical console. In some embodiments, the surgical console may further include a light source configured to project a horizontal light ray at the vertical height corresponding to the sensor strip input received from the user. In some embodiments, the PEL may be used by the surgical console to control an aspiration pump speed to increase/decrease an operating aspiration pressure to be within a desired range. As another example, the PEL may be used by the surgical console to raise/lower an irrigation bottle to increase/decrease the irrigation pressure to be within a desired range.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
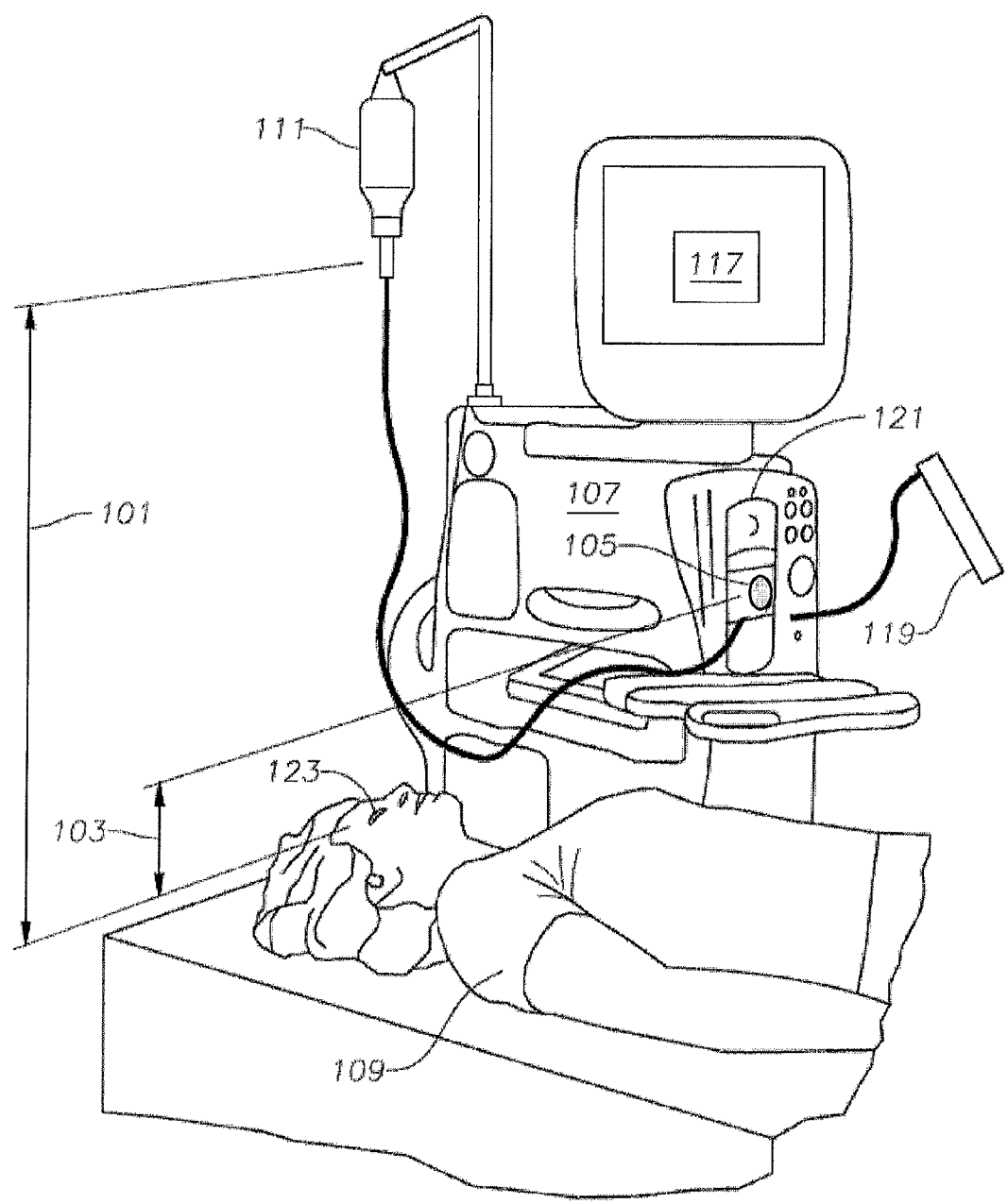
FIG. 1 illustrates patient eye level (PEL) relative to a surgical component, according to an embodiment.

FIG. 1 illustrates an embodiment of a patient eye level (PEL) 103 relative to a surgical component (e.g., an aspiration sensor 105). The PEL 103 may be a vertical height between the aspiration sensor 105 and a patient's eyes 123 when the patient 109 is lying on a surgical table 201 (see FIGS. 2a-b). As seen in FIG. 1, "vertical height" may include a perpendicular distance (e.g., in centimeters) between the patient's eyes 123 and a line, parallel to the ground/floor, that intersects the aspiration sensor 105. While several embodiments presented herein describe the PEL as a vertical height between the patient's eyes 123 and the aspiration sensor 105, it is to be understood that the PEL may also be a vertical height between the patient's eyes 123 and a different surgical component of the surgical console 107 (e.g., an irrigation sensor, irrigation bottle 111, etc.) or another reference point (e.g., the ground). In some embodiments, the PEL 103 may be used by the surgical console 107 in determining, for example, an aspiration or irrigation pressure at a patient's eyes 123. For example, an aspiration pump 121 may provide aspiration to hand piece 119 through a fluid line coupling the hand piece 119 to the console 107. In some embodiments, the surgical console 107 may determine an approximate aspiration pressure at the patient's eyes 123 (e.g., at the tip of the hand piece 119) using sensor readings at the aspiration sensor 105 (on that fluid line) in combination with the PEL. The PEL may also be used in determining an irrigation pressure. For example, irrigation pressure may increase with increasing PEL (e.g., the greater a bottle height (relative to a patient's eyes 123), the greater the pressure of irrigation fluid entering the patient's eyes 123 from the bottle 111). The surgical console 107 may use the pressure information to control a source of irrigation or aspiration (e.g., control an aspiration pump speed, an irrigation bottle height 101, etc).

Figure 2A:
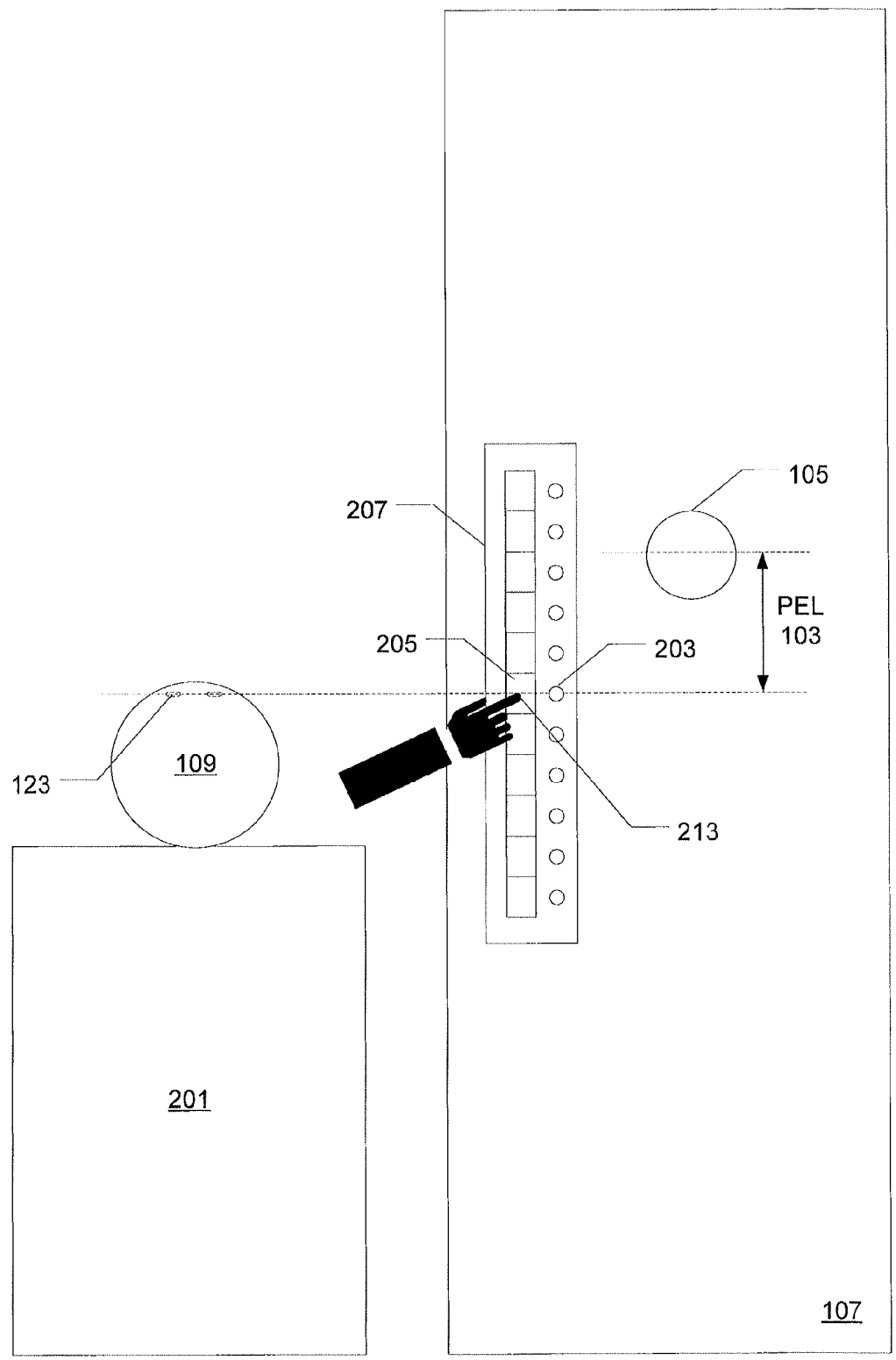
FIG. 2a illustrates a block diagram of a PEL relative to a sensor strip, according to an embodiment.

FIG. 2a illustrates a block diagram of an embodiment of PEL 103 relative to sensor strip 207. In some embodiments, a user (e.g., a surgeon, nurse, etc.) may touch (e.g., with a finger 213 or stylus) a sensor strip 207 on the surgical console 107 at a vertical height corresponding to the height of the patient's eyes 123. For example, the user may touch the sensor strip 207 at a point such that a straight line running through the point and the patient's eyes 123 is parallel to the ground/floor. The sensor strip 207 may include multiple sensors (e.g., vertically spaced) such that when a sensor (such as sensor 205) of the sensor strip 207 detects a touch, the location of the sensor strip sensor may be used to determine the PEL 103. For example, the vertical height between each sensor and the aspiration sensor 105 may be stored on a table in memory 1003 (see FIG. 7) to enable look-up of the vertical height based on the touched sensor. As another example, an equation may be used that relates the PEL with the sensor location (the sensor location (e.g., sensor height) may be an input to the equation with the PEL being the output). In some embodiments, the PEL value may be stored with the sensor strip such that when a sensor detects a touch, the corresponding PEL is automatically sent by the sensor strip to, for example, a controller on the console 107. Other PEL determination methods are also possible based on input from the sensors. Further, while the sensor strip 207 is shown on the front of the surgical console 107, other locations of the sensor strip 207 (e.g., on the side of the surgical console, etc) are also contemplated.

Figure 2B:
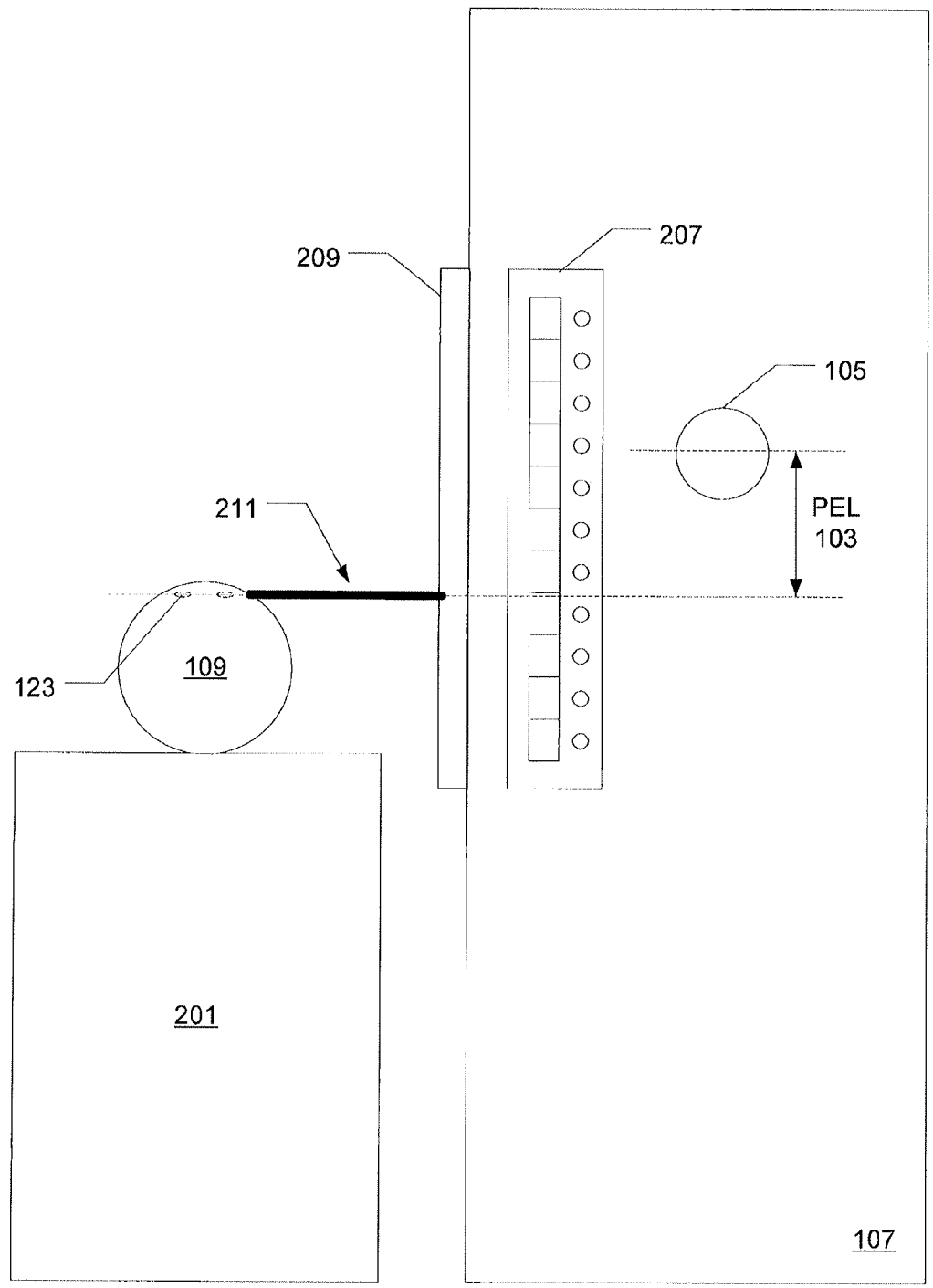
FIG. 2b illustrates a block diagram of a sensor strip and visible line projecting device, according to an embodiment.

In some embodiments, a light emitting diode (LED) 203 or other visual indicator may be used to provide the user with a visual indication of the received touch input (e.g., LED 203 may illuminate as the user touches sensor 205). The visual indication may assist the user in determining if the correct sensor strip sensor (corresponding to the intended patient eye vertical height) has been touched. In some embodiments, as seen in FIG. 2b, a visible line projecting device 209 with, for example, a row of light sources (such as a low intensity laser) or a movable light source may project a horizontal light ray 211 corresponding to the height of the touched sensor 205 toward the operating table 201. In some embodiments, the surgical console 107 may illuminate a light source (or move the movable light source) corresponding to the height of the touched sensor strip sensor. The user may determine, based on the location of the projected light ray 211 if the correct sensor strip sensor has been touched. For example, the light ray 211 may align with the patient's eyes 123 indicating that the correct height has been indicated on the sensor strip 207. In some embodiments, the light source may be a low intensity light source (e.g., a low intensity laser) to prevent damaging the patient's eyes 123. As another example, the light source may include an LED (e.g., a high-powered LED) surrounded by a reflector.

Figure 3:
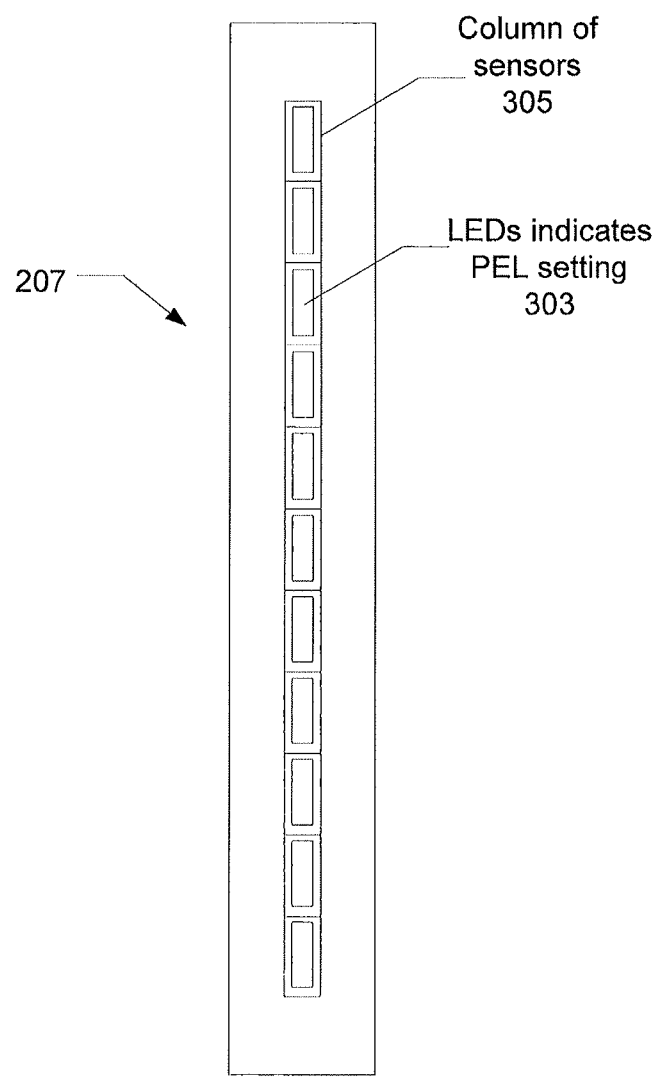
FIG. 3 illustrates a block diagram of a sensor strip with embedded light emitting diodes (LEDs), according to an embodiment.

FIG. 3 illustrates a block diagram of an embodiment of a sensor strip 207 with embedded sensors 305 and LEDs 303. In some embodiments, the sensors 305 may include sensors 305 that are sensitive to touch (e.g., field effect or capacitive sensors). The sensors 305 may be field effect switch sensors such as Touchcell™ sensors (e.g., which use low impedance electrodynamic field-effect technology) that may produce digital logic-level switching output. The field effect switch sensors may produce an electric field and detect a change in the electric field when a conductive mass (such as a human finger) enters the field. Other sensor types are also contemplated. For example, resistive sensors, buttons (e.g., a vertical array of buttons) or infrared motion detectors/cameras (to detect a relative location of the user's finger) may be used. In some embodiments, a mechanical slider (with a vertical sliding element that can be moved by the user and aligned with the patient's eyes 123) may be used. Other sensor strip sensors may also be used to receive user input indicating a vertical height of the patient's eyes 123 relative to, for example, the aspiration sensor 105. As seen in FIG. 3, the LEDs 303 may overlap the sensors 305 and may be illuminated as their respective sensor strip sensor is touched. Other locations for the LEDs are also contemplated (e.g., next to the sensor strip as shown in FIGS. 2a-b).

Figure 4:
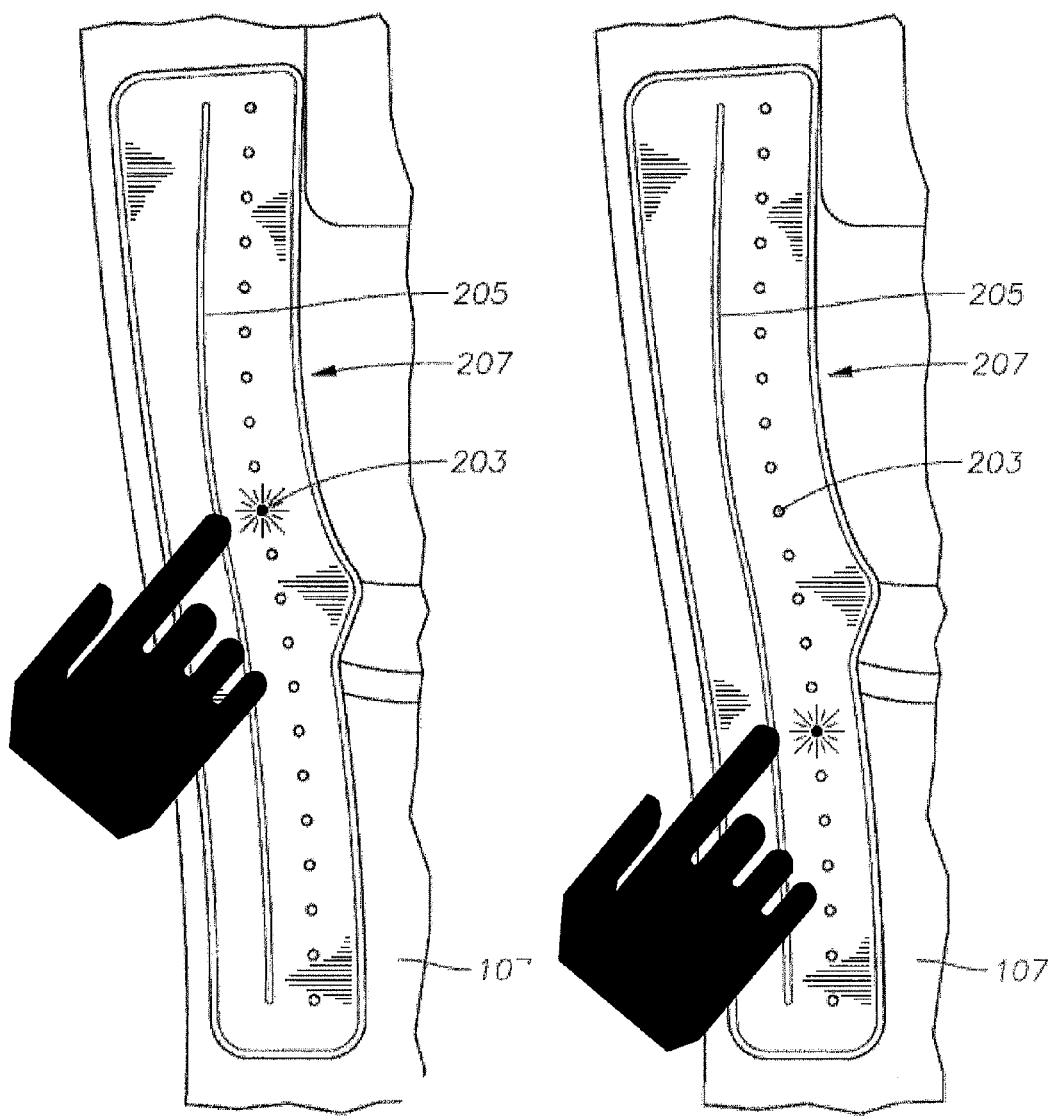
FIGS. 4a-b illustrate a user inputting a vertical height using the sensor strip, according to an embodiment.

FIGS. 4a-b illustrate an embodiment of inputting a vertical height using the sensor strip 207. As seen in FIGS. 4a-b, the sensor strip 207 may include configurations that are slanted, curved, etc. In some embodiments, distances (e.g., relative vertical heights) between the individual sensors on the sensor strip 207 and the aspiration sensor 105 may be stored (e.g., in memory 1003) such that the sensor strip 207 may take on various configurations (e.g., the sensor strip 207 may curve to follow the contour of the surgical console 107). The "vertical height" for an individual sensor strip sensor may include a perpendicular distance between the individual sensor strip sensor and a line, parallel to the ground/floor, that intersects, for example, the aspiration sensor 105. Other configurations of "height" are also contemplated. For example, the PEL may be a point along a slanted line (e.g., a line running through the aspiration sensor 205 and the patient's eyes) and calculations based on the slanted line PEL may be configured to account for location of the PEL on the slanted line (as opposed to a vertical PEL).

Figure 5:
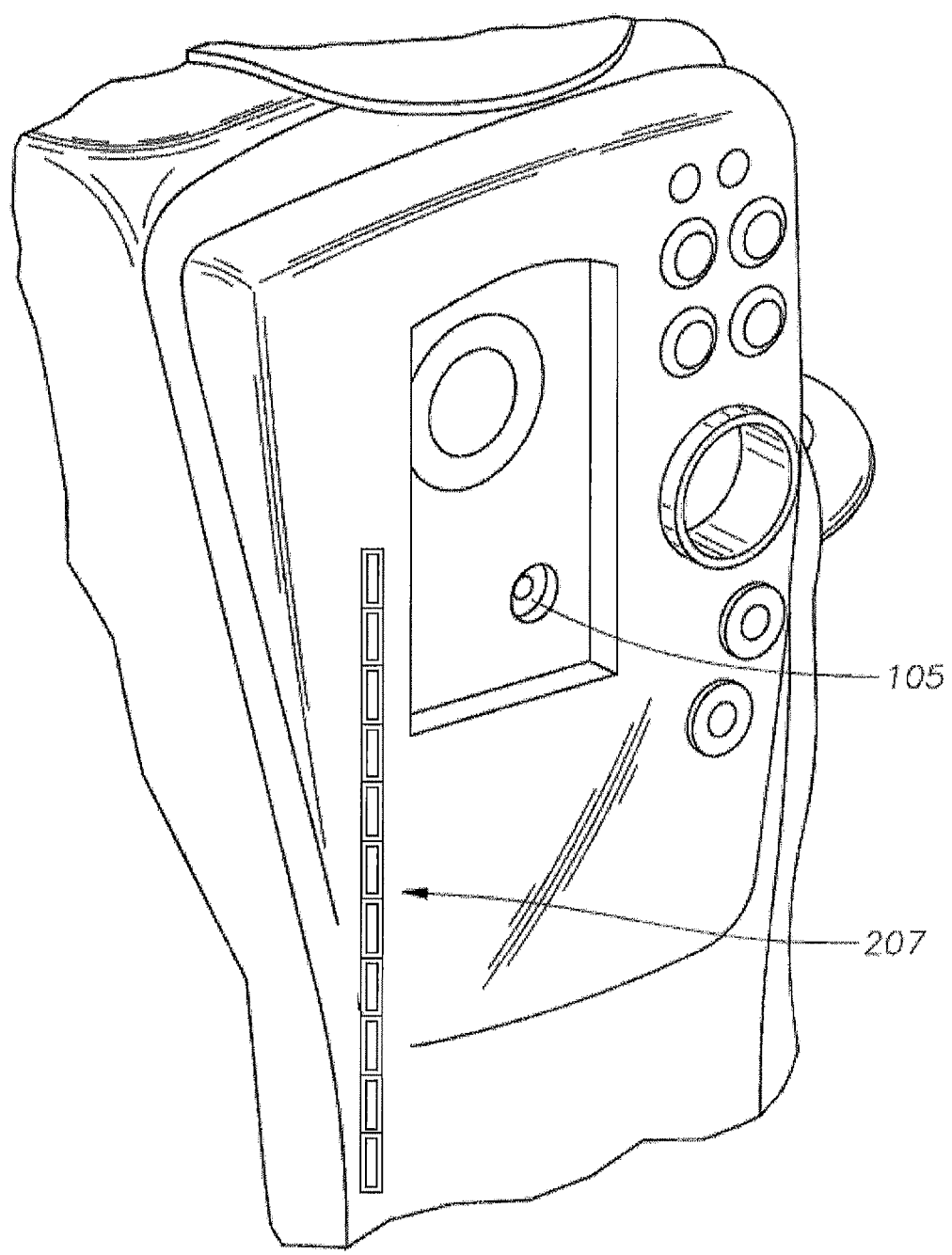
FIG. 5 illustrates a sensor strip on a surgical console, according to an embodiment.

In some embodiments, the sensor strip 207 may include a continuous slide feature (such as the continuous indentation shown in FIG. 4a) over the sensor strip sensors to assist a user in sliding their finger over the sensor strip sensors during height selection. As the user slides their finger (e.g., between FIGS. 4a and 4b) the LED associated with the touched sensor strip sensor may illuminate to indicate to a user the current sensor strip sensor location detecting the touch. FIG. 5 illustrates another embodiment of a sensor strip 207 on a surgical console. The number and placements of the sensor strip sensors may be arranged according to the desired resolution. For example, distances between sensor strip sensors may include 1 millimeter, 5 millimeters, 1 centimeter, 2 centimeters, etc. Smaller or greater distances may be used according to the desired resolution. In some embodiments, distances between sensor strip sensors may not be consistent (e.g., smaller distances may be used between sensor strip sensors located at normal patient eye levels and greater distances may be used for sensors strip sensors outside the range of normal patient eye levels).

Figure 6:
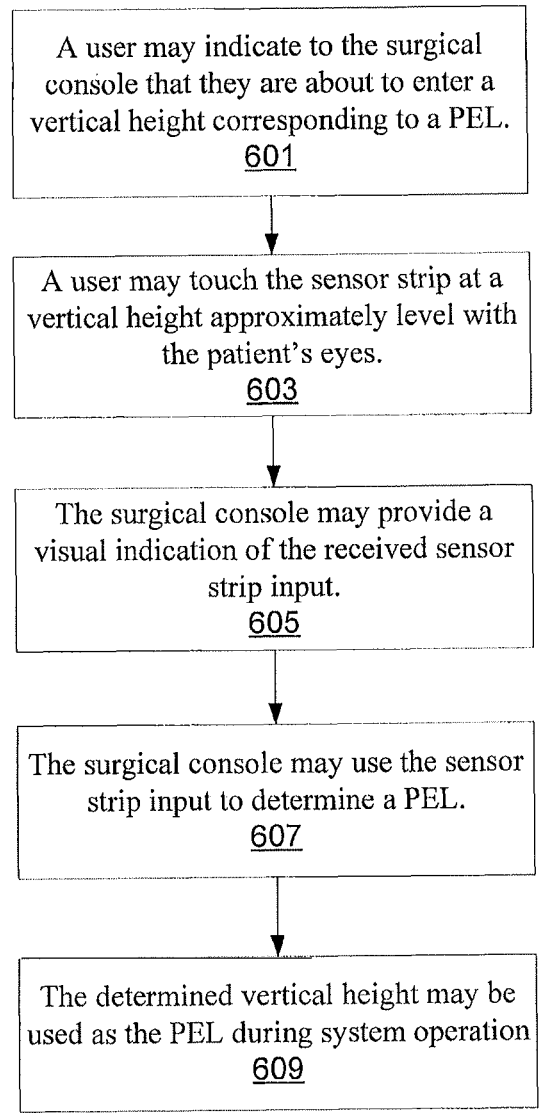
FIG. 6 illustrates a flowchart for inputting a vertical height using the sensor strip, according to an embodiment.

FIG. 6 illustrates a flowchart of an embodiment for inputting a vertical height using the sensor strip 207. The elements provided in the flowchart are illustrative only. Various provided elements may be omitted, additional elements may be added, and/or various elements may be performed in a different order than provided below.

At 601, a user may indicate to the surgical console 107 that they are about to enter a vertical height corresponding to a PEL 103. In some embodiments, the user may select an option to enter the vertical height by pressing a visual option (such as an icon) presented on a graphical user interface (GUI) 117 on the surgical console's touchscreen. Other selections mechanisms are also contemplated (keyboard, computer mouse, etc). In some embodiments, the icon may need to be selected each time a new vertical height will be indicated (i.e., the surgical console 107 may stop considering further sensor strip inputs after a vertical height is received or after a predetermined amount of time (e.g., 10 seconds) has passed since the icon was selected to prevent changes to the vertical height due to inadvertent touches). In some embodiments, the user may not need to indicate the user will be indicating a vertical height before the user enters the distance (e.g., the surgical console 107 may accept a new touch input from the sensor strip 207 at any time).

At 603, a user may touch the sensor strip 207 at a vertical height approximately level with the patient's eyes 123. In some embodiments, the user may tap the sensor strip 207 or slide their finger (or, for example, a stylus or mechanical slider) along the sensor strip 207 to the vertical height (as visually determined by the user eyeing the patient on the surgical table 201). In some embodiments, the surgical console 107 may accept the new vertical height only if the user slides their finger along multiple sensor strip sensors first to prevent the vertical location from being changed due to an inadvertent touch of the sensor strip 207. Other input indications are also contemplated (e.g., the user may be required to double tap on a sensor strip sensor corresponding to the vertical height for the input to be acknowledged by the surgical console 107).

At 605, the surgical console 107 may provide a visual indication of the received sensor strip input. For example, the surgical console 107 may illuminate an LED 203 or project a horizontal line (e.g., laser) toward the patient 109 corresponding to the touched sensor strip sensor (or last touched sensor strip sensor if a user slides their finger along the sensor strip). Other visual indicators are also contemplated.

At 607, the surgical console 107 may use the sensor strip input to determine a PEL 103. For example, a table 1005 with sensor strip sensor identifications and the relative vertical heights between the sensor strip sensors and the aspiration sensor 105 may be accessed to determine a vertical height between the sensor detecting a touch and the aspiration sensor 105. As another example, the vertical heights (between the sensor strip sensors and the aspiration sensor 105) corresponding to each sensor strip sensor may be stored in a one to one correlation (e.g., stored with the sensor strip sensors) that is not necessarily in table format. In some embodiments, multiple PELs (e.g., relative to multiple console components) may be determined. For example, a table with vertical heights relative to the each individual sensor strip sensor and components such as the irrigation bottle, irrigation sensor, aspiration sensor, etc. may be used to determine PELs relative to other system components based on a single sensor strip input.

At 609, the determined vertical height may be used as the PEL during system operation (e.g., in determining irrigation and aspiration pressure). For example, the PEL may be used along with input from the aspiration sensor 105 to determine a relative aspiration pressure at the patient's eyes 123. As another example, a PEL (relative to an irrigation bottle) may be used to determine an irrigation pressure at the patient's eyes 123. The respective aspiration and/or irrigation pressures may be used to control an aspiration pump speed (to increase/decrease the aspiration pressure to be within a desired range) or raise/lower the irrigation bottle (to increase/decrease the irrigation pressure to be within a desired range). Other PEL uses are also possible.

Figure 7:
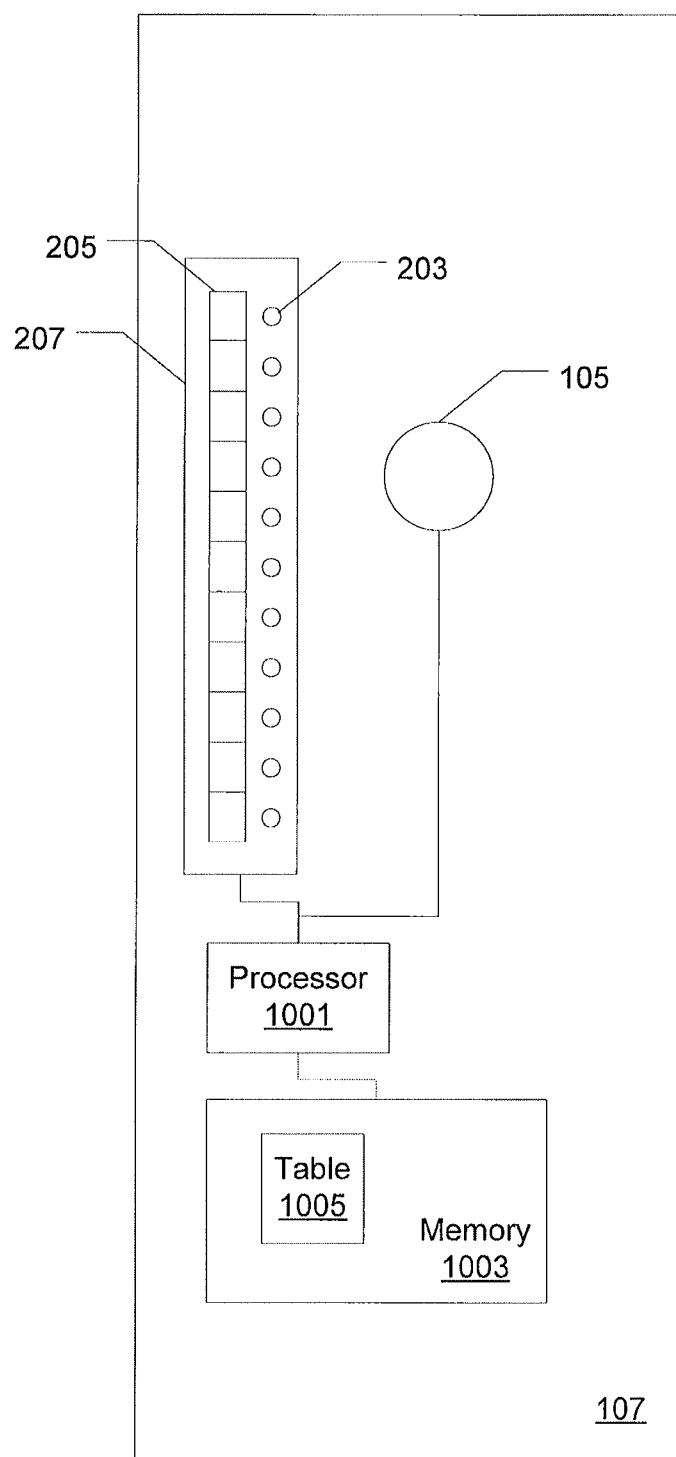
FIG. 7 illustrates a console with a sensor strip and processor, according to an embodiment.

In some embodiments, as seen in FIG. 7, the surgical console may include one or more processors (e.g., processor 1001). The processor 1001 may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory 1003 coupled to and/or embedded in the processors 1001 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors 1001 implement one or more of its functions via a state machine, analog circuitry, digital circuitry, and/or logic circuitry, the memory 1003 storing the corresponding operational instructions may be embedded within, or external to, the circuitry comprising the state machine, analog circuitry, digital circuitry, and/or logic circuitry. The memory 1003 may store, and the processor 1001 may execute, operational instructions corresponding to at least some of the elements illustrated and described in association with the figures. For example, the processor 1001 may process touch inputs (e.g., relayed as digital values) from the sensor strip sensor to determine a PEL 103 for use with pressure measured by the aspiration pressure sensor 105.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A surgical console, comprising:
   at least one component configured to be used during an ophthalmic surgical procedure;
   a sensor strip comprising a plurality of sensor strip sensors, wherein at least two of the plurality of sensor strip sensors are offset vertically and wherein the sensor strip is configured to receive an input from a user, through the sensor strip, at an input point on the sensor strip that aligns with a vertical height of a patient's eyes relative to the surgical console such that a line, parallel to a ground/floor supporting the surgical console, intersects the input point on the sensor strip and the patient's eyes;
   wherein the surgical console is configured to use the input to determine a patient eye level (PEL) relative to the at least one component;
   wherein the surgical console is configured to use the PEL and the at least one component in controlling operation of at least one of a source of irrigation or a source of aspiration during the ophthalmic surgical procedure.

2. The surgical console of claim 1, wherein the plurality of sensor strip sensors comprise field effect switch or capacitive sensors.

3. The surgical console of claim 1, wherein the PEL is a perpendicular distance between the patient's eyes and the line, parallel to the ground/floor, that intersects the at least one component of the surgical console.

4. The surgical console of claim 1, further comprising a plurality of visual indicators, wherein at least two of the plurality of visual indicators are positioned relative to at least two of the plurality of sensor strip sensors.

5. The surgical console of claim 4, wherein the surgical console is configured to illuminate at least one of the plurality of visual indicators that corresponds to a sensor detecting the touch input.

6. The surgical console of claim 1, wherein the at least one component of the surgical console is an aspiration pressure sensor.

7. The surgical console of claim 1, wherein the plurality of sensor strip sensors are arranged along a curved line on the surgical console.

8. The surgical console of claim 1, wherein the PEL is used by the surgical console to control an aspiration pump speed to increase/decrease an operating aspiration pressure to be within a desired range.

9. The surgical console of claim 1, wherein the PEL is used by the surgical console to raise/lower the source of irrigation to increase/decrease an irrigation pressure provided through a hand piece coupled to the surgical console to be within a desired range.

10. The surgical console of claim 1, further comprising a light source configured to project a horizontal light ray at the vertical height corresponding to the sensor strip input received from the user.

11. A surgical console, comprising:
an aspiration pump;
an aspiration sensor configured to detect an aspiration pressure in a line coupled to the aspiration pump;
a sensor strip comprising a plurality of field effect switch or capacitive sensors, wherein at least two of the plurality of sensor strip sensors are offset vertically and wherein the sensor strip is configured to receive an input from a user, through the sensor strip, at an input point on the sensor strip that aligns with a vertical height of a patient's eyes relative to the surgical console such that a line, parallel to a ground/floor supporting the surgical console, intersects the input point on the sensor strip and the patient's eyes;
a plurality of visual indicators, wherein at least two of the plurality of visual indicators are positioned relative to the at least two of the plurality of sensor strip sensors and wherein the surgical console is configured to illuminate at least one of the plurality of visual indicators that corresponds to a sensor strip sensor detecting the user input;
wherein the surgical console is configured to use the input to determine a patient eye level (PEL) relative to the aspiration sensor of the surgical console;
wherein the surgical console is configured to use the PEL and information from the aspiration sensor to control operation of the aspiration pump to obtain a desired aspiration pressure at the patient's eyes through a hand piece coupled to the surgical console.

12. The surgical console of claim 6, wherein the sensor strip and the aspiration pressure sensor are fixed relative to each other on a main body of the surgical console.

13. The surgical console of claim 11, wherein the PEL is a perpendicular distance between the patient's eyes and the line, parallel to the ground/floor, that intersects the aspiration sensor of the surgical console.

14. The surgical console of claim 11, wherein the plurality of visual indicators overlap the plurality of sensor strip sensors.

15. The surgical console of claim 11, wherein the plurality of sensor strip sensors and the plurality of visual indicators are arranged along a curved line on the surgical console.

16. The surgical console of claim 11, wherein the PEL is further used by the surgical console to raise/lower the irrigation bottle to increase/decrease an irrigation pressure provided through a hand piece coupled to the surgical console to be within a desired range.

17. The surgical console of claim 11, further comprising a light source configured to project a horizontal light ray at the vertical height corresponding to the sensor strip input received from the user.

18. The surgical console of claim 11, wherein the sensor strip and the aspiration sensor are fixed relative to each other on a main body of the surgical console.

* * * * *